United States Patent
Imai et al.

(10) Patent No.: US 7,873,141 B2
(45) Date of Patent: Jan. 18, 2011

(54) X-RAY TOMOGRAPHIC IMAGING APPARATUS

(75) Inventors: Yasuhiro Imai, Tokyo (JP); Akihiko Nishide, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 502 days.

(21) Appl. No.: 11/944,262

(22) Filed: Nov. 21, 2007

(65) Prior Publication Data

US 2008/0260092 A1    Oct. 23, 2008

(30) Foreign Application Priority Data

Nov. 22, 2006    (JP) .............................. 2006-316030

(51) Int. Cl.
    *A61B 6/00*    (2006.01)
(52) U.S. Cl. ...................... 378/5; 378/98.11; 378/98.12
(58) Field of Classification Search .................... 378/5, 378/98.11, 98.12
    See application file for complete search history.

(56) References Cited

U.S. PATENT DOCUMENTS

| | | | |
|---|---|---|---|
| 4,361,901 A | | 11/1982 | Daniels |
| 4,542,459 A | * | 9/1985 | Riederer ...................... 600/431 |
| 4,813,061 A | | 3/1989 | Kakegawa |
| 4,868,857 A | | 9/1989 | Dobbins, III |
| 4,896,037 A | * | 1/1990 | Shimura et al. ............. 250/583 |
| 5,049,748 A | | 9/1991 | Ito |
| 5,376,795 A | | 12/1994 | Hasegawa et al. |
| 5,570,403 A | | 10/1996 | Yamazaki et al. |

(Continued)

FOREIGN PATENT DOCUMENTS

DE    3712639 A    10/1987

(Continued)

OTHER PUBLICATIONS

German Patent and Trademark Office, Translation of Official Action in 10 2007 053 511.4-35, Dec. 1, 2009, 7 pages.

(Continued)

*Primary Examiner*—Edward J Glick
*Assistant Examiner*—Alexander H Taningco
(74) *Attorney, Agent, or Firm*—Armstrong Teasdale LLP

(57) ABSTRACT

For the purpose of providing an X-ray tomographic imaging apparatus for displaying a dual-energy image to facilitate diagnosis by an operator, an X-ray tomographic imaging apparatus (10) comprises: an image comparison information calculating section (24) for calculating image comparison information between said first-energy projection dataset(LD) or first-energy tomographic image(LT) and said second-energy projection dataset(HD) or second-energy tomographic image(HT); a region-of-interest defining section (23) for defining a region of interest; a weighting factor determining section (25-2) for determining a weighting factor for use in weighted subtraction processing between said first-energy projection dataset or first-energy tomographic image and said second-energy projection dataset or second-energy tomographic image, such that said image comparison information in said region of interest can be substantially eliminated by conducting said weighted subtraction processing; and a dual-energy image reconstructing section (22) for reconstructing a dual-energy image by conducting weighted subtraction processing between said first-energy projection dataset or first-energy tomographic image and said second-energy projection dataset or second-energy tomographic image used in said image comparison information calculating section, using a weighting factor determined at said weighting factor determining section.

20 Claims, 10 Drawing Sheets

U.S. PATENT DOCUMENTS

| | | |
|---|---|---|
| 6,343,111 B1 | 1/2002 | Avinash et al. |
| 6,421,419 B1 * | 7/2002 | Sakaida .................. 378/98.11 |
| 6,661,873 B2 | 12/2003 | Jabri et al. |
| 7,203,274 B2 | 4/2007 | Charles, Jr. et al. |
| 2001/0038682 A1 * | 11/2001 | Salb .......................... 378/98.9 |
| 2002/0085671 A1 * | 7/2002 | Sakaida .................. 378/98.11 |
| 2003/0095630 A1 * | 5/2003 | Avinash et al. ............. 378/98.9 |
| 2003/0142787 A1 | 7/2003 | Jabri et al. |
| 2003/0147497 A1 | 8/2003 | Avinash |
| 2006/0109949 A1 * | 5/2006 | Tkaczyk et al. ................ 378/4 |
| 2006/0227929 A1 * | 10/2006 | Takanezawa et al. ........... 378/5 |
| 2009/0135994 A1 * | 5/2009 | Yu et al. ........................ 378/5 |

FOREIGN PATENT DOCUMENTS

| | | |
|---|---|---|
| DE | 102004055460 A1 | 4/2006 |
| JP | 57-111998 | 12/1982 |
| JP | 03-133275 | 6/1991 |
| JP | 2003-099808 | 4/2003 |
| JP | 2003-244542 | 8/2003 |
| JP | 2006-142020 | 6/2006 |

OTHER PUBLICATIONS

Netherlands Foreign Search Report, Octrooiaanvrage Nr: 1034728, Rapport Betreffende Het Onderzoek Naar De Stand Van De Techniek, Aug. 13, 2008.

* cited by examiner (a)

(b)

(a)

(b)

(a)

(b)

(a)

(b)

X-RAY TOMOGRAPHIC IMAGING APPARATUS

CROSS REFERENCE TO RELATED APPLICATIONS

This application claims the benefit of Japanese Patent Application No. 2006-316030 filed Nov. 22, 2006.

BACKGROUND OF THE INVENTION

The present invention relates to an X-ray tomographic imaging technology, and particularly to an X-ray tomographic imaging apparatus pertinent to dual-energy imaging.

In dual-energy imaging, an image can be acquired with a specific material within a subject to be examined highlighted based on X-ray projection data for the imaged subject acquired with X-rays having two different energy spectra. Specifically, an image acquired with high-energy X-rays and that acquired with low-energy X-rays are subjected to addition/subtraction processing, whereby a dual-energy image clearly showing bones and calcified lesions or that clearly showing soft tissue can be obtained.

In performing dual-energy imaging, the projection data acquired with high-energy X-rays and those acquired with low-energy X-rays are obtained by alternately switching the tube voltage for X-rays emitted by an X-ray imaging apparatus between a high voltage and a low voltage for each scan, or by replacing an X-ray filter to change the X-ray energy. For example, Japanese Patent Application Laid Open No. 2003-244542 discloses an invention comprising displaying an image representing bones or that representing soft tissue based on an image acquired with high-energy X-rays and that acquired with low-energy X-rays. To obtain an image of bones or soft tissue, the invention employs a weighting factor that is predetermined according to atoms of bones (calcium) or the like.

SUMMARY OF THE INVENTION

The weighting factor for use in weighted subtraction processing for obtaining an image of bones or soft tissue, however, is not always constant because of a difference in size among subjects and a difference in X-ray absorption coefficient due to individual differences among subjects. If diagnosis is made with a dual-energy image using a constant weighting factor without considering an influence of the difference in size among subjects, etc., overestimation or underestimation of a disease or injury may consequently occur.

Therefore one aspect of the present invention is to provide an X-ray tomographic imaging apparatus in which an appropriate weighting factor can be set for every subject and for every region in a subject. Moreover, another aspect of the present invention is to provide an X-ray tomographic imaging apparatus capable of displaying an image that is quantitatively and visually comprehensible using an appropriate weighting factor.

An X-ray tomographic imaging apparatus in a first aspect is an X-ray tomographic imaging apparatus for obtaining a dual-energy image based on a first-energy projection dataset or a first-energy tomographic image with X-rays of a first energy and a second-energy projection dataset or a second-energy tomographic image with X-rays of a second energy different from said first energy, comprising: an image comparison information calculating section for calculating image comparison information between said first-energy projection dataset or first-energy tomographic image and said second-energy projection dataset or second-energy tomographic image; a region-of-interest defining section for defining a region of interest; a weighting factor determining section for determining a weighting factor for use in weighted subtraction processing between said first-energy projection dataset or first-energy tomographic image and said second-energy projection dataset or second-energy tomographic image, such that said image comparison information in said region of interest can be substantially eliminated by conducting said weighted subtraction processing; and a dual-energy image reconstructing section for reconstructing a dual-energy image by conducting weighted subtraction processing between said first-energy projection dataset or first-energy tomographic image and said second-energy projection dataset or second-energy tomographic image used in said image comparison information calculating section, using a weighting factor determined at said weighting factor determining section.

The weighting factor for use in obtaining an image of bones or that of soft tissue varies with a difference in size among subjects. FIG. 10 shows a study of the relationship of the ratio of pixel values between tomographic images containing fat, calcium and iodine, where the horizontal axis corresponds to a tube voltage of 140 kV, and the vertical axis corresponds to a tube voltage of 80 kV. It can be seen that the respective ratios of pixel values for the materials are different between phantoms having a cross-sectional area of 700 cm2 (as shown in FIG. 10(a)) and 300 cm2 (as shown in FIG. 10(b)), due to a difference in cross-sectional area. The ratios of pixel values can be roughly predicted for phantoms. However, subjects to be examined have different ratios of pixel values due to, in addition to a difference in cross-sectional area, the shape of a cross section, and a difference in X-ray absorption coefficient caused by individual differences and the like. Thus, inaccurate ratios of pixel values may lead to overestimation or underestimation of a disease or injury.

The X-ray tomographic imaging apparatus in the first aspect has the weighting factor determining section that determines a weighting factor such that image comparison information in a region of interest defined at the region-of-interest defining section can be substantially eliminated. Then, the dual-energy image reconstructing section reconstructs a dual-energy image with the weighting factor, and thus an image that is quantitatively and visually comprehensible can be displayed.

The X-ray tomographic imaging apparatus in a second aspect comprises the image comparison information calculating section that reconstructs a comparison image by subtraction processing between the first-energy projection dataset or first-energy tomographic image and the second-energy projection dataset or second-energy tomographic image, and calculates an image characteristic quantity of the comparison image as the image comparison information.

Since by this configuration, the image characteristic quantity for a comparison image can be obtained as the image comparison information, the image characteristic quantity for a comparison image and a weighting factor can be easily determined.

The X-ray tomographic imaging apparatus in a third aspect is that of a second aspect, further comprising an image display section for displaying the comparison image, wherein the region-of-interest defining section enables the region of interest to be defined based on a comparison image displayed on the image display section.

By this configuration, a human operator can conveniently define a region of interest based on a comparison image that the operator desires to diagnose, by displaying it on the image display section.

In a fourth aspect, the X-ray tomographic imaging apparatus of the second or third aspect further comprises: an image characteristic quantity display section for displaying an image characteristic quantity varying with variation of the weighting factor, wherein the weighting factor determining section comprises a weighting factor adjusting section enabling manual modification of the weighting factor while viewing variation of the displayed image characteristic quantity.

By this configuration, an operator can manually adjust the weighting factor via the weighting factor adjusting section while viewing variation of the image characteristic quantity displayed on the image characteristic quantity display section, in addition to viewing the comparison image. In particular, a slider bar or the like may be used to adjust the weighting factor.

The X-ray tomographic imaging apparatus in a fifth aspect is that of the fourth aspect, wherein: the image characteristic quantity is an average value or median value of pixel values for pixels within a region of interest in the comparison image, and the weighting factor determining section determines a weighting factor when the image characteristic quantity becomes zero or falls within a certain range in proximity of zero, as a weighting factor for the region of interest.

By this configuration, an average value or median value of a comparison image within a region of interest can be used as an image characteristic quantity of the region of interest to set a proper value for the weighting factor. A median value is a central value of values in a comparison image within a region of interest when the values are arranged in an ascending (or descending) order. Moreover, obtained is an image that can be substantially eliminated if the image characteristic quantity is zero or falls within a certain range in proximity of zero.

The X-ray tomographic imaging apparatus in a sixth aspect comprises the image comparison information calculating section that calculates a ratio of pixel values between the first-energy projection dataset or first-energy tomographic image and the second-energy projection dataset or second-energy tomographic image as the image comparison information, and the region-of-interest defining section extracts a region having similar ratios of pixel values as a region of interest.

By this configuration, the weighting factor can be automatically modified through a distribution of ratios of pixel values between the first-energy projection dataset or first-energy tomographic image and the second-energy projection dataset or second-energy tomographic image. In practice, a weighting factor is automatically determined from a tomographic image acquired by imaging the subject with X-rays. Specifically, the weighting factor can be determined taking account of the cross-sectional area, the shape of a cross section, and a difference in X-ray absorption coefficient caused by the individual difference and the like, of a subject. Since diagnosis can be made using a dual-energy image calculated with an accurate weighting factor, a disease or injury can be accurately evaluated.

The X-ray tomographic imaging apparatus in a seventh aspect comprises the weighting factor determining section in the sixth aspect that determines the weighting factor based on a peak value of a distribution of ratios of pixel values between the first-energy projection dataset or first-energy tomographic image and the second-energy projection dataset or second-energy tomographic image in the region of interest.

By this configuration, the weighting factor is determined based on a peak value in a distribution of ratios of pixel values of an actually taken image, whereby a dual-energy image of equivalent images for the peak value can be obtained. For example, the peak value can be found from a differential value of a histogram of the distribution.

The X-ray tomographic imaging apparatus in an eighth aspect further comprises a colored display section for coloring the region of interest, and displaying it superimposed over the first-energy tomographic image or the second-energy tomographic image.

By this configuration, since a region of interest is colored, the operator, who makes diagnosis while observing a dual-energy image, can make diagnosis while perceiving the region of interest.

The X-ray tomographic imaging apparatus in a ninth aspect is that in the eighth aspect, wherein the colored display section is capable of displaying a plurality of different regions of interest in one subject in different colors.

By this configuration, two or more regions of interest can be identified with different colors and one can make diagnosis while simultaneously observing the two or more regions of interest. For example, water is displayed in blue, and calcium is displayed in yellow.

The X-ray tomographic imaging apparatus in a tenth aspect further comprises: a colored display section for conducting coloring with the color tone varying with the ratio of pixel values between the first-energy projection dataset or first-energy tomographic image and the second-energy projection dataset or second-energy tomographic image.

By this configuration, a region of interest is colored according to a ratio of pixel values, and the operator, who makes diagnosis while observing a dual-energy image, can make diagnosis while perceiving the region of interest.

According to the present invention, an operator, who makes diagnosis while observing a dual-energy image, can know an accurate weighting factor required to obtain a dual-energy image. Thus, a specific material (atoms) to be diagnosed in imaging of a dual-energy image, such as, for example, a contrast agent, fat or calcium within a subject, can be accurately perceived for diagnosis.

DETAILED DESCRIPTION OF THE INVENTION

Configuration of an X-Ray Tomographic Imaging Apparatus.

Figure 1:
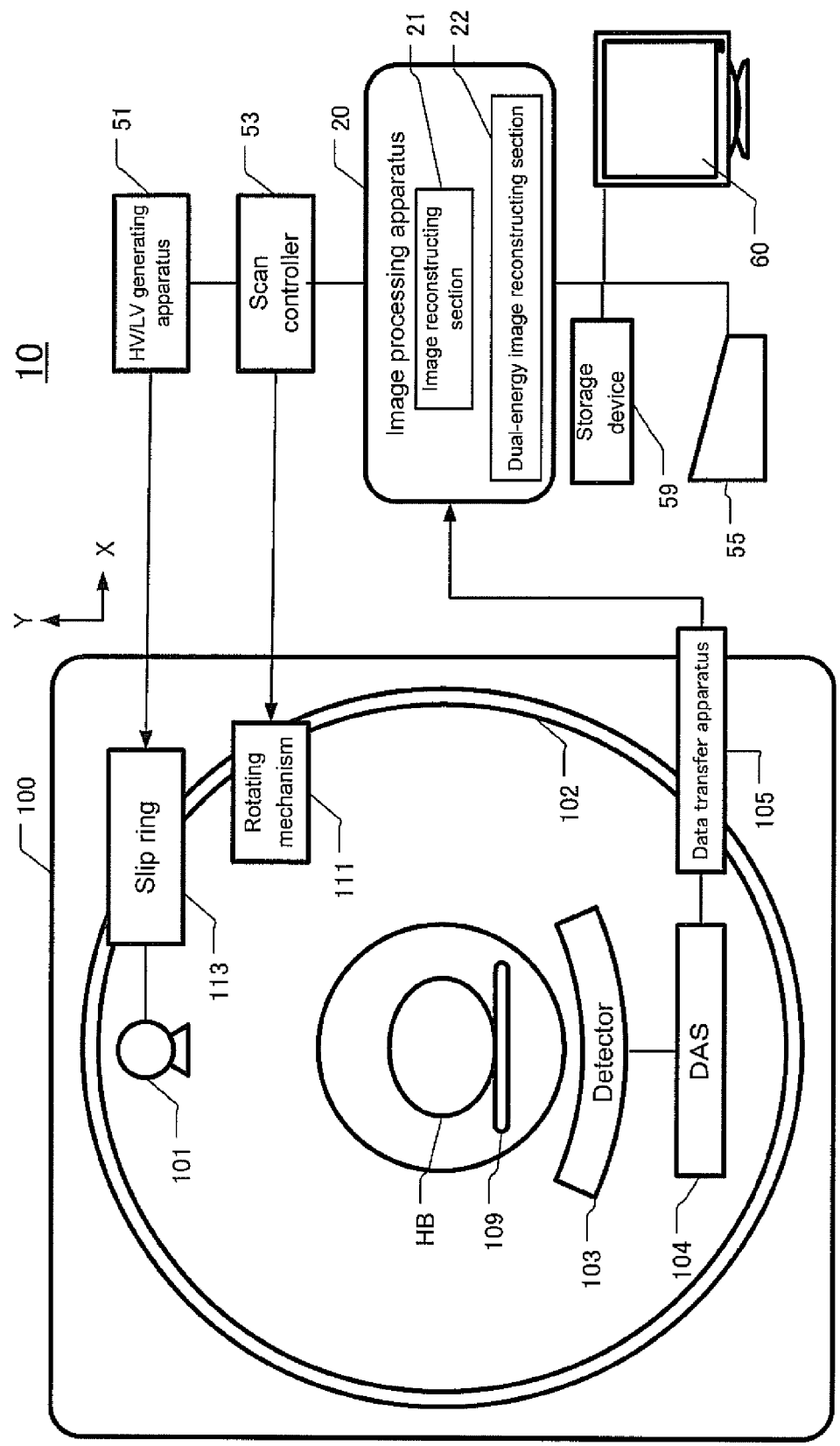
FIG. 1 is a block diagram showing the configuration of an X-ray CT apparatus 10 in accordance with the present embodiment.

FIG. 1 is a block diagram showing the configuration of an X-ray tomographic imaging apparatus (X-ray CT apparatus) 10 in accordance with an embodiment of the present invention. The X-ray tomographic imaging apparatus 10 is provided with a gantry 100, and a table 109 for inserting a subject HB into an imaging region in the gantry 100. The table 109 is moved in a Z-direction, which is a direction of a body axis of the subject HB. The gantry 100 has a rotating ring 102, which comprises an X-ray tube 101 for emitting X-rays of a cone beam shape and a multi-row X-ray detector 103 disposed to face the X-ray tube 101. The X-ray tube 101 is configured to emit X-rays having a high-energy spectrum and those having a low-energy spectrum. The multi-row X-ray detector 103 detects X-rays passing through the subject HB.

The multi-row X-ray detector 103 is formed of scintillators and photodiodes. The multi-row X-ray detector 103 is arranged to form a plurality of rows in the Z-direction that is generally parallel to the axis of rotation of the rotating ring 102 so that a plurality of slices (rows) of projection data can be simultaneously detected. The multi-row X-ray detector 103 also has a multi-channel form arranged in an arc centering a focal spot of the X-ray tube 101. It should be noted that the Z-direction that is parallel to the axis of rotation will be sometimes referred to as "slice direction," and the direction along the arc of an X-ray detector element row as "channel direction." The multi-row X-ray detector 103 is connected with a data collecting circuit 104, which is generally referred to as a DAS (data acquisition system). The data collecting circuit 104 is provided for each channel thereof with an I-V converter for converting an electric current signal from each channel in the multi-row X-ray detector 103 into a voltage, an integrator for periodically integrating the voltage signal in synchronization with the cycle of X-ray emission, an amplifier for amplifying the signals output from the integrator, and an analog-to-digital converter for converting output signals from the preamplifier into digital signals. The digital signals from the data collecting circuit 104 are sent to an image processing apparatus 20 via a data transfer apparatus 105.

On the operator console side, a high voltage (HV)/low voltage (LV) generator 51 for energizing the X-rays is provided. The high voltage/low voltage generator 51 periodically generates high voltage and low voltage, and supply them to the X-ray tube 101 via a slip ring 113.

A scan controller 53 on the operator console side executes a plurality of scan patterns including an axial scan, a helical scan, a variable-pitch helical scan, etc. An axial scan is a scan method involving acquiring projection data while rotating the X-ray tube 101 and X-ray detecting section 103 by a rotating mechanism 111 each time the table 109 is moved at a prespecified pitch in the Z-axis direction. A helical scan is a scan method involving acquiring projection data while moving the table 109 at a prespecified speed and rotating the X-ray tube 101 and X-ray detecting section 103. A variable-pitch helical scan is a scan method involving acquiring projection data at a varying speed of the table 109 while rotating the X-ray tube 101 and X-ray detecting section 103 by the rotating mechanism 111, as in the helical scan. The scan controller 53 drives the rotating mechanism 111 in synchronization with the high voltage/low voltage generator 51 to integrally control a scan, including periodical collection of projection data by the data collecting circuit 104 and the like.

The image processing apparatus 20 comprises an image reconstructing section 21 and a dual-energy image reconstructing section 22.

The image reconstructing section 21 receives a low-energy projection dataset LD or a high-energy projection dataset HD, and reconstructs an image based on the low-energy projection dataset LD or high-energy projection dataset HD. The low-energy projection dataset LD or high-energy projection dataset HD is subjected to fast Fourier transform (FFT) for conversion into a frequency domain, and is multiplied by a reconstruction function and inversely Fourier-transformed. The projection data convoluted with the reconstruction function is subjected to three-dimensional backprojection processing to produce a tomographic image (in an xy-plane) in a body axis direction (Z-direction) of the subject HB. The tomographic image is stored in a storage device 59 and also is displayed on a display 60. Since in this embodiment, the X-ray tube 101 emits X-rays having a low-energy spectrum and those having a high-energy spectrum toward the subject HB, the image reconstructing section 21 reconstructs a high-energy tomographic image HT from the X-rays of a high-energy spectrum and a low-energy tomographic image LT from the X-rays of a low-energy spectrum.

The dual-energy image reconstructing section 22 produces a dual-energy image DI by multiplying one or both of an image of the projection dataset HD of a high-energy spectrum and an image of the projection dataset LD of a low-energy spectrum by a weighting factor, applying subtraction between the projection datasets, and reconstructing the weighted and subtracted projection data into an image. The dual-energy image reconstructing section 22 is also capable of reconstructing a dual-energy image DI by multiplying one or both of the tomographic image HT of a high-energy spectrum and the tomographic image LT of a low-energy spectrum by a weighting factor, and applying subtraction between the images. The dual-energy image DI will be discussed later with reference to FIG. 3.

An input device 55 is comprised of a keyboard or a mouse for accepting an input by the operator.

The storage device 59 stores programs, X-ray detector data, projection data, and X-ray tomographic images. It also stores the dual-energy image DI.

The display 60 is for specifying imaging conditions for a subject, and displaying an X-ray tomographic image. In this embodiment, it also displays a dual-energy image DI with a specific material in the subject highlighted by a color.

Operation of the X-Ray Tomographic Imaging Apparatus.

Figure 2:
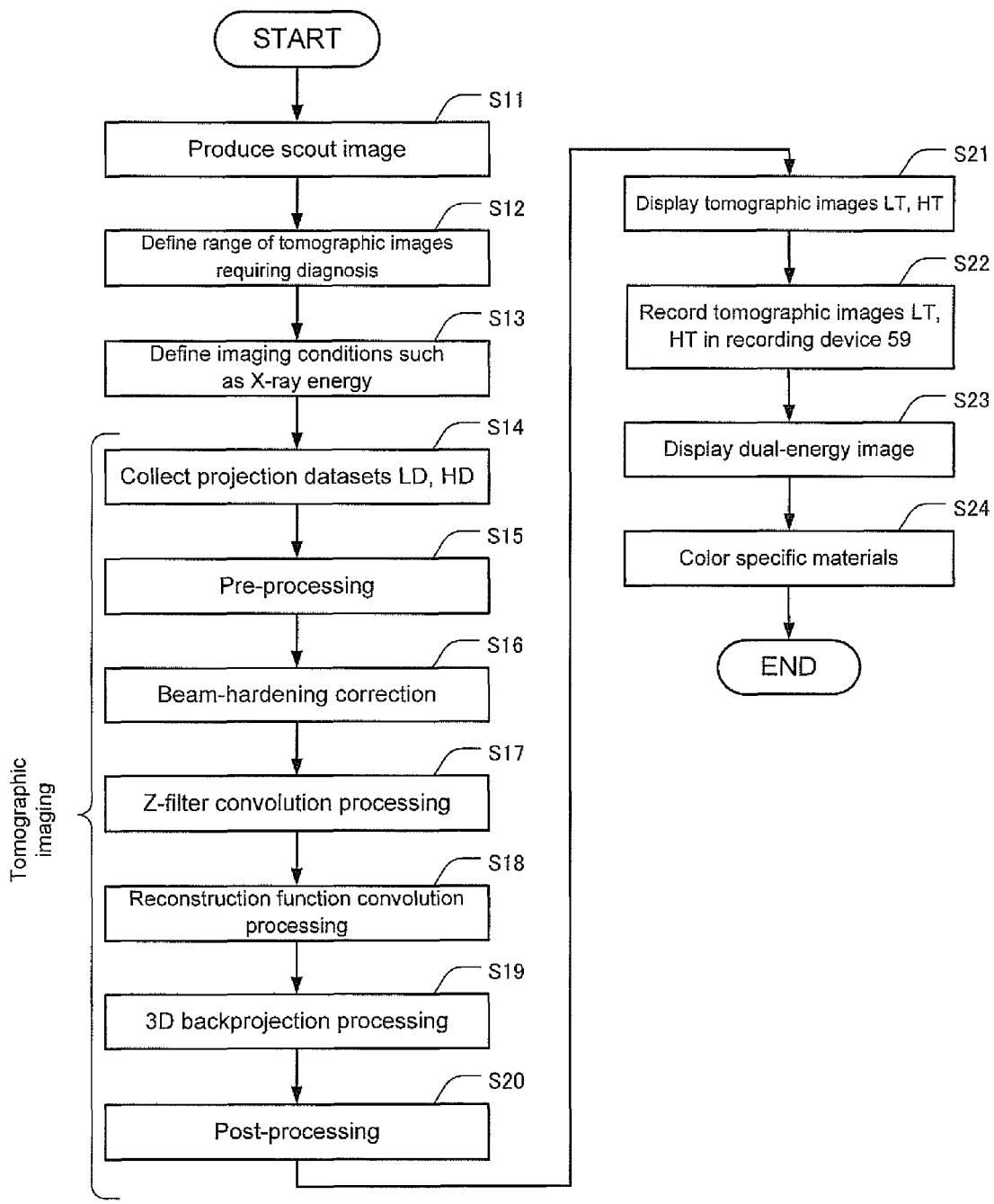
FIG. 2 is a flow chart of an operation of the X-ray tomographic imaging apparatus 10.

FIG. 2 is a flow chart of an operation of the X-ray tomographic imaging apparatus 10. Now a procedure for the operation of the X-ray tomographic imaging apparatus 10 in accordance with an embodiment of the present invention will be described hereinbelow.

At Step S11, a subject is laid on the table 109 and positioned in place. A reference point in a certain region in the subject laid on the table 109 is aligned with a slice center position in the gantry 100. Then, a scout image (which is also referred to as scanogram or X-ray fluoroscopic image) is collected. Two kinds of scout images can be captured according to the size of the subject, i.e., for an adult or a child, and the images are usually captured at 0 deg. and 90 deg. In some regions such as the head, for example, only a 90-deg scout image may be acquired. In the scout imaging, data collection is operated with the X-ray tube 101 and multi-row X-ray detector 103 fixed, while translating the table 109.

At Step S12, the operator uses a keyboard etc. in the input device 55 to define a position and a range on a scout image displayed on the display 60 for a tomographic image to be captured in the following tomographic imaging. At that time, a setting of an axial scan, a helical scan, a cine scan, a variable-pitch helical scan or a helical shuttle scan is also made. A variable-pitch helical scan is an imaging method for collecting X-ray projection data while rotating the X-ray tube 101 and multi-row X-ray detector 103 and moving the table 109, as in a helical scan, wherein the speed is variable. A helical shuttle scan is a scan method for collecting X-ray projection data while rotating the X-ray tube 101 and multi-row X-ray detector 103, and reciprocally moving the table 109 in positive and negative directions along the Z-axis with acceleration and deceleration.

At Step S13, conditions for tomographic imaging or those for imaging of a dual-energy image DI are specified. For the X-ray tube 101 to emit X-rays having a high-energy spectrum and those having a low-energy spectrum toward the subject HB, the high voltage and low voltage are set to 140 kV and 80 kV, respectively, for example. Moreover, to prevent positional offset as much as possible, a setting is made for alternately emitting X-rays with a high voltage and those with a low voltage in synchronization with rotations of the rotating mechanism 111. For example, a setting for the X-ray tube 101 repeatedly alternating high and low voltages for every revolution of the X-ray tube 101, or a setting for repeatedly alternating high and low voltages in a cycle of short pulses may be contemplated.

Furthermore, at Step S13, a specific material (atoms) to be diagnosed in imaging of a dual-energy image DI is specified. For example, a contrast agent, fat, calcium or the like within the subject is specified. In addition, a filter function, a Kernel function or the like in image reconstruction is specified. These specified conditions are recorded in the storage device 59. It should be noted that although in this embodiment, high-energy spectrum and low-energy spectrum are generated by voltage, the energy spectrum may be modulated by inserting a filter into the cone-beam X-rays.

In Steps S14-S20, Tomographic Imaging is Conducted.

At Step S14, an X-ray projection dataset LD of a low-energy spectrum and an X-ray projection dataset HD of a high-energy spectrum are collected. If data collection is performed in a conventional scan, the operation of data collection of X-ray detector data is performed with the table 109 fixed, while rotating the X-ray tube 101 and multi-row X-ray detector 103 around the subject. Then, the X-ray detector data D0(view, j, i) represented by the view angle view, detector row index j and channel index i (j=1–ROW, and i=1–CH) is appended with a z-direction coordinate position Ztable (view).

At Step S15, a low-energy projection dataset LD0(view, j, i) and a high-energy projection dataset HD0(view, j, i) are pre-processed. In particular, offset correction is applied, logarithm conversion is made, X-ray dose correction is applied, and then sensitivity correction is applied.

At Step S16, the pre-processed low-energy projection dataset LD(view, j, i) and high-energy projection dataset HD(view, j, i) are subjected to beam-hardening correction.

At Step S17, the image reconstructing section 21 performs z-filter convolution processing. Here, z-filter convolution processing, in which a filter in a z-direction (row direction) is applied, is performed on the beam-hardening corrected projection datasets. Specifically, after pre-processing at each view angle and in each X-ray data collection system, a row direction filter is applied to the beam-hardening corrected projection datasets D from the multi-row X-ray detector, in the row direction.

At Step S18, the image reconstructing section 21 performs reconstruction function convolution processing. Specifically, the X-ray projection datasets D are Fourier-transformed into a frequency domain, multiplied by a reconstruction function, and then inversely Fourier-transformed. In the reconstruction function convolution processing, a reconstruction function Kernel(j) is convoluted.

At Step S19, the image reconstructing section 21 performs three-dimensional backprojection processing. Here, three-dimensional backprojection processing is performed on the projection datasets D subjected to reconstruction function convolution processing to obtain backprojected datasets. An image to be reconstructed is three-dimensionally reconstructed in an xy-plane that is vertical to the Z-axis. A reconstruction region P in the following description is considered to be parallel to the xy-plane.

At Step S20, the image reconstructing section 21 performs post-processing. The backprojected datasets are subjected to post-processing, including image filter convolution and CT value conversion, to obtain a tomographic image HT of a high-energy spectrum and a tomographic image LT of a low-energy spectrum.

At Step S21, the reconstructed tomographic image HT of a high-energy spectrum and tomographic image LT of a low-energy spectrum are displayed on the display 60.

Then, at Step S22, these tomographic images HT and LT are stored in the storage device 59.

At Step S23, the dual-energy image reconstructing section 22 displays a dual-energy image DI on the display 60.

Then, at Step S24, a colored display section 28, which will be discussed later, puts colors over the tomographic images HT and LT, using a color for each specific material, such as the same atomic material, fat, water, calcium, iodine contrast agent, or the like.

Image Reconstruction for a Dual-Energy Image DI.

Figure 3:
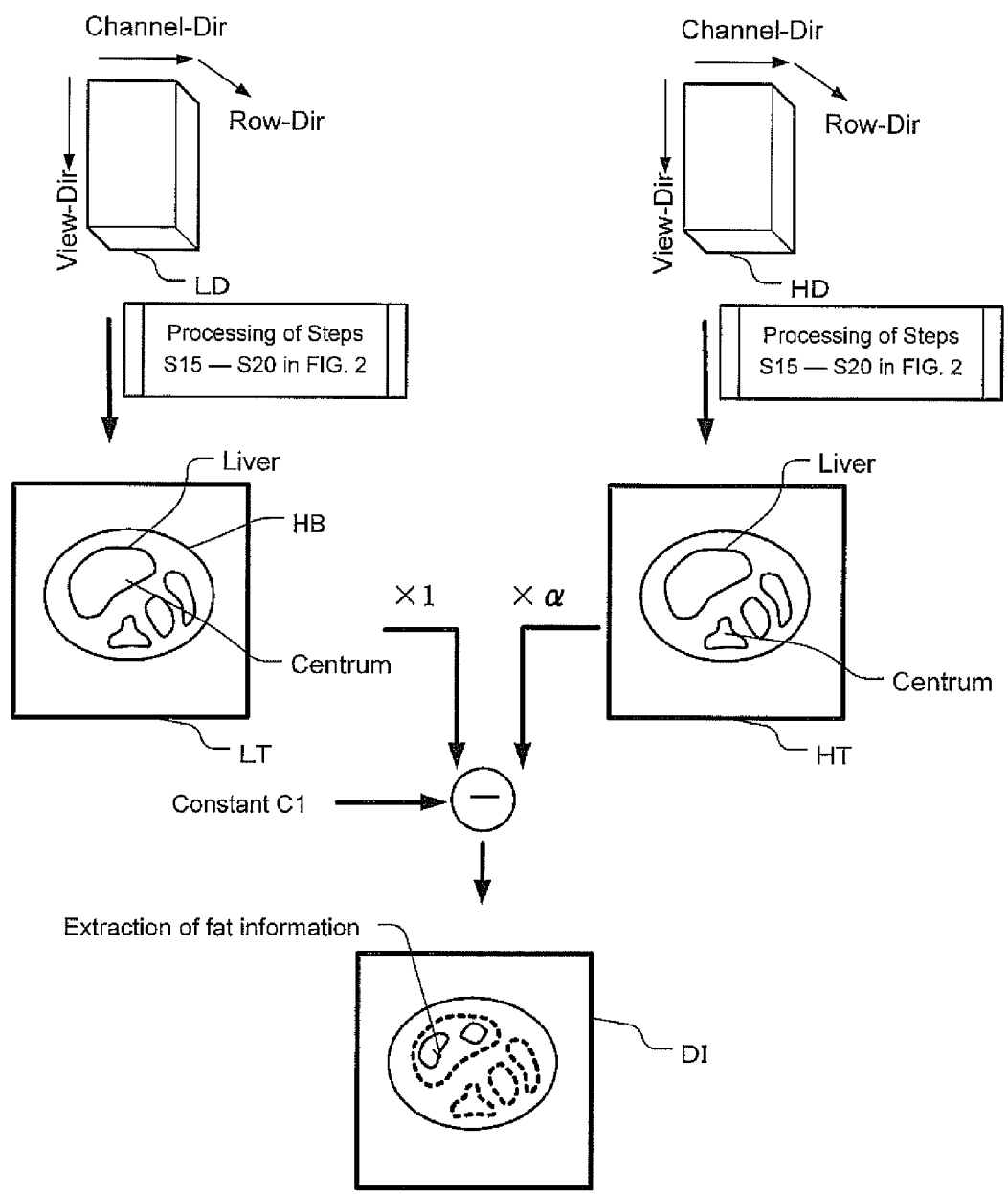
FIG. 3 is a conceptual diagram showing a tomographic image HT of a high-energy spectrum or a tomographic image LT of a low-energy spectrum subjected to weighted subtraction processing to produce a dual-energy image DI.

FIG. 3 is a conceptual diagram showing a tomographic image HT of a high-energy spectrum or a tomographic image LT of a low-energy spectrum to be subjected to weighted subtraction processing to obtain a dual-energy image DI.

Dual-energy imaging involves weighted subtraction processing between a tomographic image LT at a low X-ray tube voltage, e.g., 80 kV, and a tomographic image HT at a high X-ray tube voltage, e.g., 140 kV, at a certain z -direction coordinate position, to thereby produce a tomographic image DI that is a quantitative image of a distribution of a desired material.

In the upper portion of FIG. 3, an X-ray projection dataset LD of a low-energy spectrum and an X-ray projection dataset HD of a high-energy spectrum are first obtained, as described above for Step S14 in FIG. 2.

Next, the image reconstructing section 21 performs the processing of Steps S15-Step S20 as described above with reference to FIG. 2 on the low-energy projection dataset LD and high-energy projection dataset HD to reconstruct a tomographic image LT of a low-energy spectrum and a tomographic image HT of a high-energy spectrum.

In the lower portion of FIG. 3, the dual-energy image reconstructing section 22 multiplies the tomographic image LT of a low-energy spectrum by a weighting factor one, and the tomographic image HT of a high-energy spectrum by a weighting factor α, and performs weighted subtraction processing along with a constant C1. A dual-energy image DI can thus be obtained. The weighting factor α and constant C1 are determined depending upon atoms to be extracted, atoms to be highlighted, and atoms or a region to be eliminated in a display. Taking the reciprocal of α, it is possible to define the weighting factor for the tomographic image LT of a low-energy spectrum as α, and that for the tomographic image HT of a high-energy spectrum as one. In FIG. 3, extraction of fat information is shown.

Rather than obtaining a dual-energy image DI from the tomographic image LT of a low-energy spectrum and a tomographic image HT of a high-energy spectrum, the dual-energy image DI may be obtained by applying weighted subtraction processing to an X-ray projection dataset LD collected at a low X-ray tube voltage and an X-ray projection dataset HD collected at a high X-ray tube voltage, and reconstructing the weighted-subtraction processed X-ray projection datasets into an image.

FIG. 4(a) is a diagram depicting the subject HB in a three-dimensional image, and FIG. 4(b) shows the view of (a) taken through an xz-plane.

A dual-energy image DI of a plurality of cross-sectional planes T (including a tomographic image LT of a low-energy spectrum and a tomographic image HT of a high-energy spectrum) is stored in the storage device 59, and tomographic images T of the cross-sectional planes can be combined to display a volume-rendered three-dimensional image 31, as shown in FIG. 4(a). Likewise, a three-dimensional image for the dual-energy image DI can be displayed.

A coronal image 33 shown in FIG. 4(b) is an image of (a) taken through a coronal plane (xz-plane) 33; thus, a dual-energy image DI in any arbitrary coronal plane can be obtained. Moreover, although not shown, it is possible to obtain a dual-energy image DI in a sagittal plane (yz-plane) 34, and also obtain a dual-energy image DI in a cross section in any arbitrary direction including an oblique direction. The operator can appropriately use any dual-energy image DI suitable for diagnosis.

Weight Setting Method.

Manual Weighting Factor Setting Method.

FIG. 5(a) is a block diagram of the image processing apparatus 20 for practicing a manual weight setting method, and FIG. 5(b) shows an example of a display for the operator manually setting an appropriate weighting factor while displaying a comparison image, i.e., a dual-energy image DI, on the display 60. This is a method for manually optimizing a difference in size among subjects HB, a difference in X-ray absorption coefficient due to individual differences among the subjects HB, or the like.

In manually setting a weighting factor, the image processing apparatus 20 is comprised of the image reconstructing section 21, the dual-energy image reconstructing section 22, a first region-of-interest defining section 23-1, a first image comparison information calculating section 24-1, a weighting factor adjusting section 25-1, an image characteristic quantity display section 27, and the colored display section 28, as shown in FIG. 5(a). Since the image reconstructing section 21 and dual-energy image reconstructing section 22 have been described earlier, description thereof will be omitted.

The first region-of-interest defining section 23-1 allows the operator to define part of a region of a comparison image acquired at the first image comparison information calculating section 24-1, which will be discussed later, displayed on the display 60, as a region of interest ROI to be reviewed. The operator arbitrarily define the region of interest ROI using a mouse, which is one of the components in the input device 55.

The first image comparison information calculating section 24-1 first reconstructs a comparison image obtained by subtraction processing between the low-energy X-ray projection dataset LD or low-energy tomographic image LT and high-energy X-ray projection dataset HD or high-energy tomographic image HT. The comparison image may be obtained by multiplying one or both of them by a weighting factor determined beforehand according to atoms or materials and then subtracting one from the other, or may be a differential image without multiplication with a weighting factor. It should be noted that image reconstruction for the comparison image may be executed at the dual-energy image reconstructing section 22. Next, an image characteristic quantity for the aforementioned comparison image is calculated for a region of interest ROI defined at the first region-of-interest defining section 23-1. The calculation of the image characteristic quantity may be applied to the entire comparison image and then only information on the region of interest ROI may be extracted; or the calculation may be applied to only the region of interest ROI. Furthermore, the image characteristic quantity includes an average value or median value of pixels defined in the region of interest ROI. It should be noted that a median value of pixels is a central pixel value of pixel values in the defined region of interest ROI.

The weighting factor adjusting section 25-1 is an adjusting section for allowing the operator to adjust a weighting factor for use in obtaining a dual-energy image DI. The operator determines a weighting factor to be multiplied with at least one or both of the high-energy projection dataset HD or high-energy tomographic image HT and low-energy projection dataset LD or low-energy tomographic image LT.

The image characteristic quantity display section 27 displays an image characteristic quantity 165 calculated by the first image comparison information calculating section 24-1.

The colored display section 28 is configured to apply the same color to the same atomic material, that is, a material having the same X-ray absorptivity, and a different color to a different atomic material. In particular, a pixel identified as fat, calcium and iodine contrast agent are colored in red, blue and green, respectively, for display on the display 60.

Figure 5:
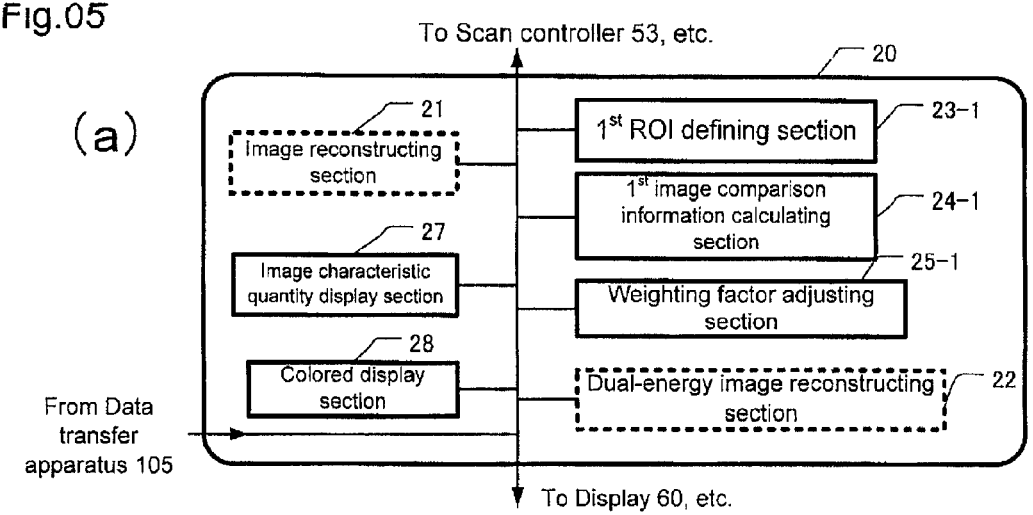
FIG. 5(a) is a block diagram of an image processing apparatus 20 for manually setting a weighting factor.
FIG. 5(b) shows an example of a display for the operator manually setting an appropriate weighting factor while viewing a dual-energy image DI on a display 60.
Figure 5:
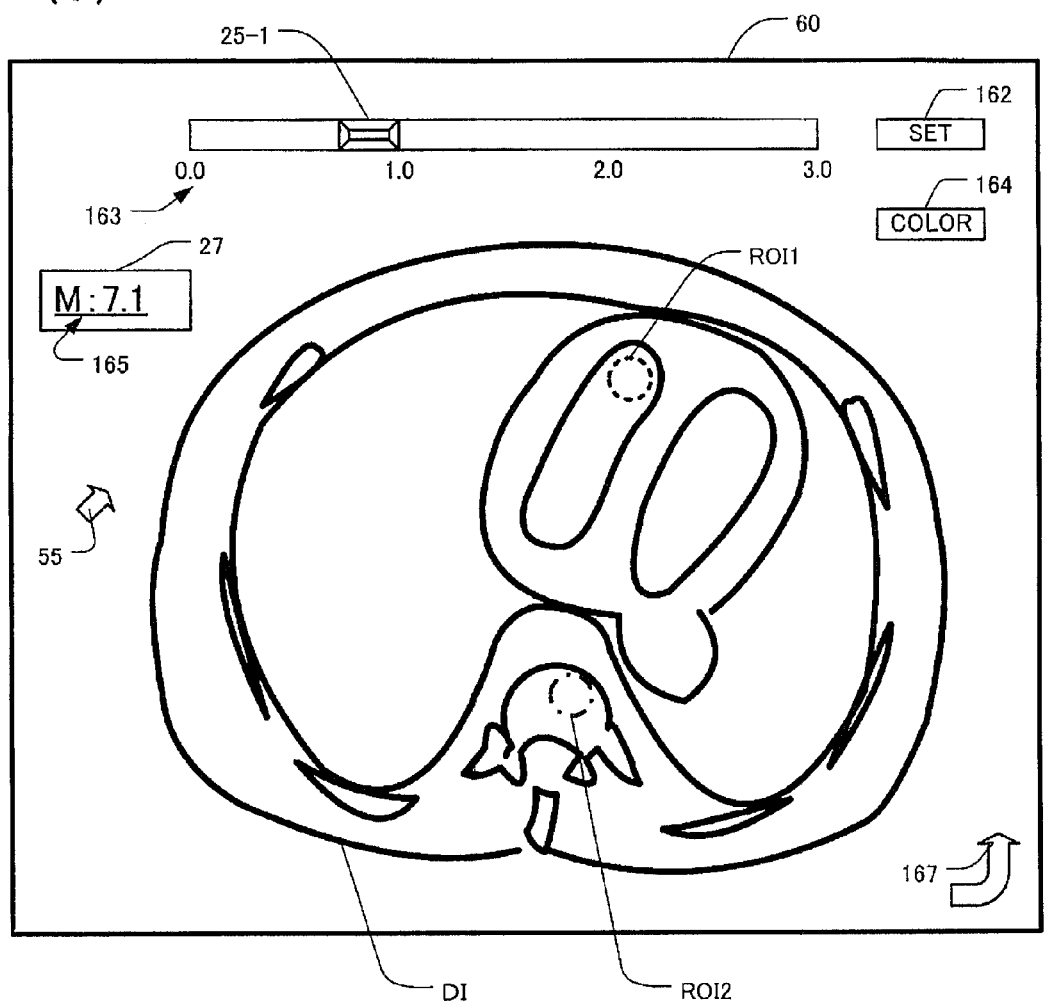

The first region-of-interest defining section 23-1 displays a viewport for defining a region of interest on the display 60 as shown in FIG. 5(b). The operator operates a mouse in the input device 55 to define a region of interest ROI1 on the display 60 in part of a displayed comparison image. The size of the region of interest ROI1 can be arbitrarily defined, and it is not limited to a certain size, or to a circular shape. In FIG. 5, the region of interest ROI1 is defined in a heart. Once the region of interest ROI1 has been defined, the first image comparison information calculating section 24-1 calculates an image characteristic quantity 165 for pixels in the region of interest ROI1. The image characteristic quantity display section 27 displays the result of the calculation, i.e., M 7.1, around the dual-energy image DI, as shown in FIG. 5. If the image characteristic quantity 165 is an average value in the region of interest ROI1 in the comparison image, "M 3.0" is displayed, for example; and if it is a median value in the region of interest ROI1 in the comparison image, "C 3.0" is displayed. Choice between the average value and median value is at the operator's option.

Next, the operator moves the weighting factor adjusting section 25-1, particularly, a slider bar, to the right or left such that the value of the image characteristic quantity 165 becomes zero or falls within a certain range in proximity of zero. Below the slider bar, there is shown a marking 163. The marking 163 designates the weighting factor α. That is, the operator can use the slider bar to arbitrarily adjust the weighting factor (which will be described later with reference to the aforementioned weighting factor α). Although the marking 163 is shown to designate the weighting factor from 0 to 3, a weighting factor ranging from 0.5 to 2.5 is sufficient if the X-ray tube 101 is operated at a tube voltage of 140 kV and 80 kV to display a dual-energy image DI. The slider bar 161 shown in FIG. 5 points to 0.9. The marking 163 may be automatically updated depending upon a combination of high-energy X-rays and low-energy X-rays. Moreover, although the slider bar 161 is shown in FIG. 5, the weighting factor α may be directly input via a keyboard, which is one of the components in the input device 55.

Upon adjustment of the weighting factor α by the operator using the slider bar, the first image comparison information calculating section 24-1 recalculates the image characteristic quantity 165 for pixels in the region of interest ROI1 using the weighting factor α as adjusted. Moreover, the dual-energy image reconstructing section 22 reconstructs a comparison image using the adjusted weighting factor α, and at the same time, the dual-energy image DI is altered. The operator checks the image characteristic quantity displayed in the image characteristic quantity display section 27 as to whether or not the image characteristic quantity 165 becomes zero or falls within a certain range from zero, or adjusts the weighting factor α using the slider bar while viewing the comparison image. Once adjustment of the weighting factor α has been completed, the operator can press a SET button 162 to terminate the manual setting of the weighting factor. When the SET button 162 is pressed, a frame indicating the region of interest ROI1 (shown by a dotted line in FIG. 5(b)) disappears. Furthermore, when a COLOR button 164 is pressed, the colored display section 28 colors pixels having a value of zero or a value falling within a certain range from zero, as in the region of interest ROI1, superimposed over one of the low-energy tomographic image LT or tomographic image HT of a high-energy spectrum. For example, when an iodine contrast agent has a value of zero in the region of interest ROI1, the heart, aorta, blood vessels and the like containing the iodine contrast agent is colored in red.

The operator may define another region of interest ROI2, in addition to the region of interest ROI1, in the comparison image displayed on the display 60. The first region-of-interest defining section 23-1 defines in FIG. 5 the spine portion as a frame indicating the region of interest ROI2 (shown by a dot-dash line in FIG. 5(b)). Then, the operator adjusts the slider bar 161 such that the image characteristic quantity 165 for the region of interest ROI2 becomes zero or falls within a certain range from zero, as described above. The operator presses a RETURN button 167 to change over to the viewport to another after completing all settings.

Figure 6:
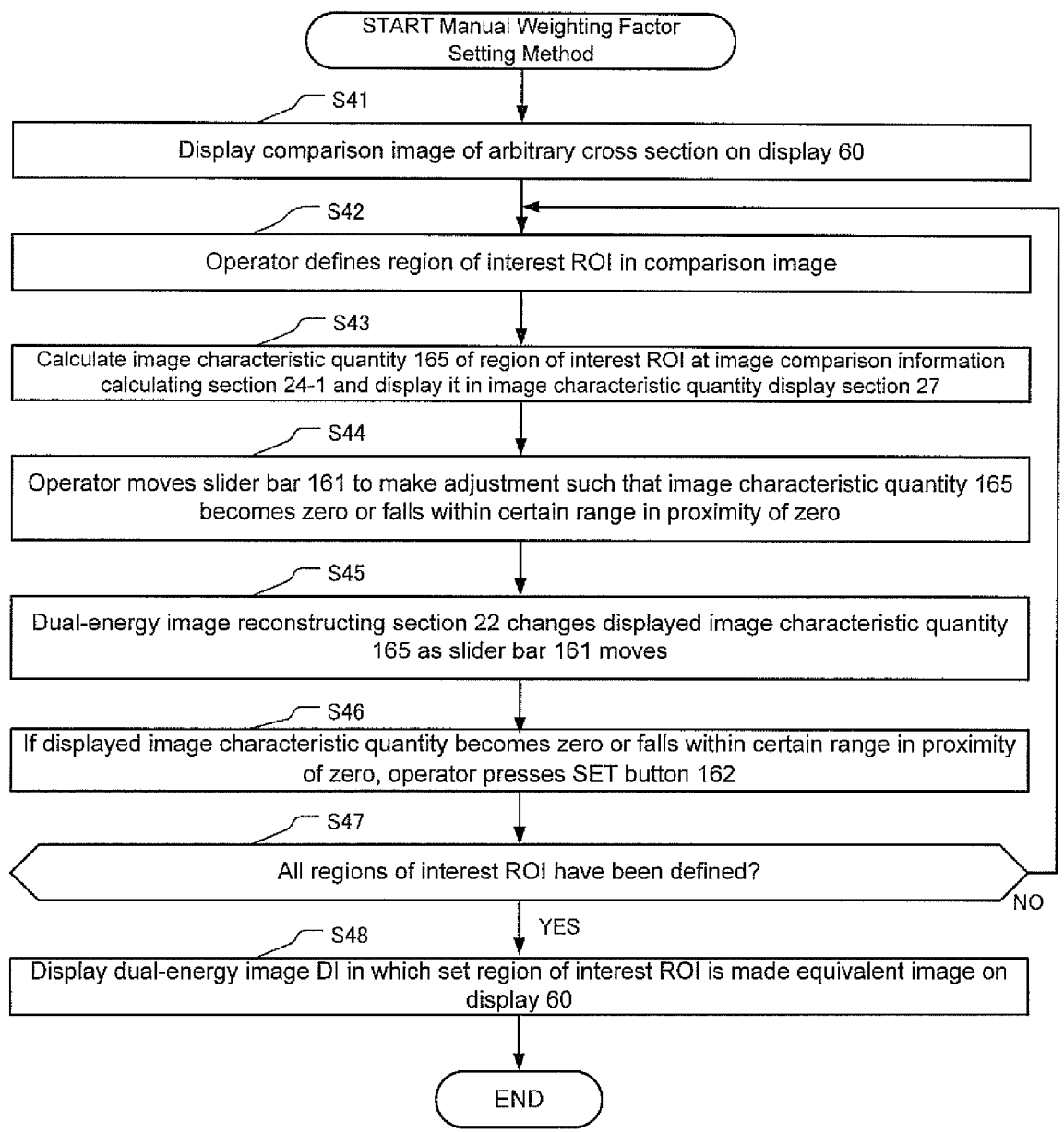
FIG. 6 is a flow chart for the operator manually setting an appropriate weighting factor.

FIG. 6 is a flow chart for the operator manually adjusting the weighting factor to an appropriate value as described above with reference to FIG. 5. That is, it is a flow chart for an operator manually adjusting a weighting factor to an appropriate value.

Figure 4:
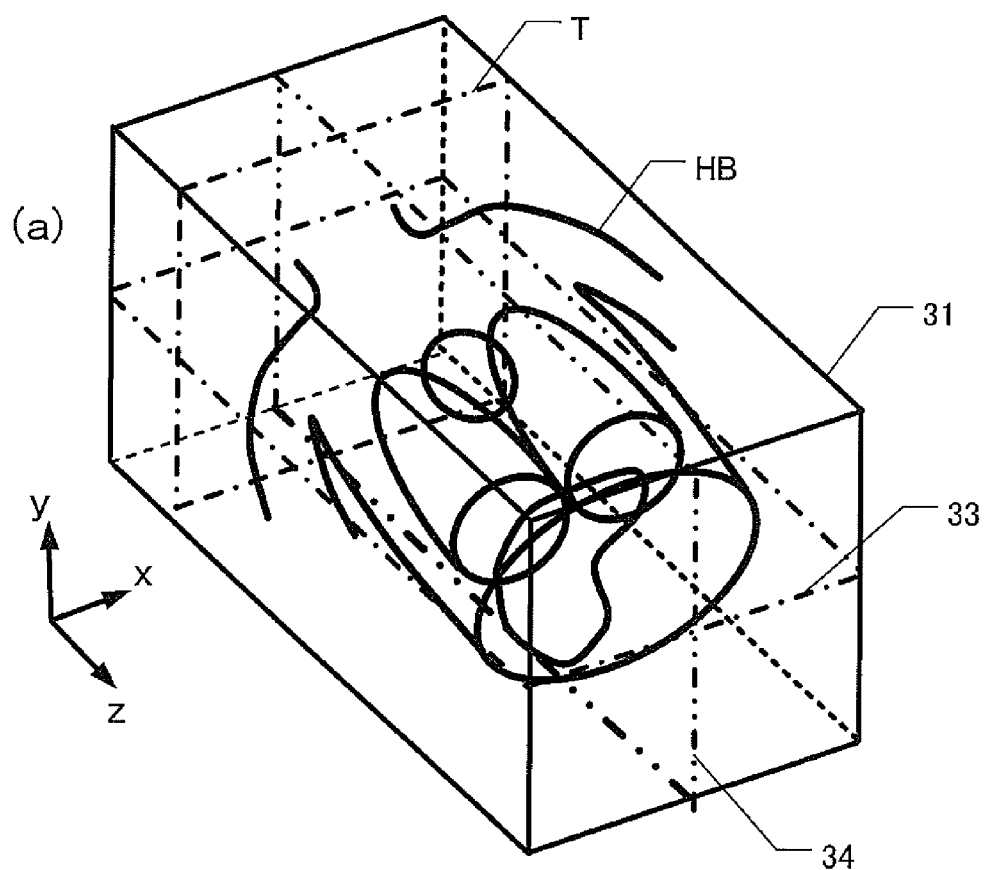
FIG. 4(a) is a diagram depicting a subject HB in a three-dimensional image.
FIG. 4(b) shows FIG. 4(a) taken through an xz-plane.
Figure 4:
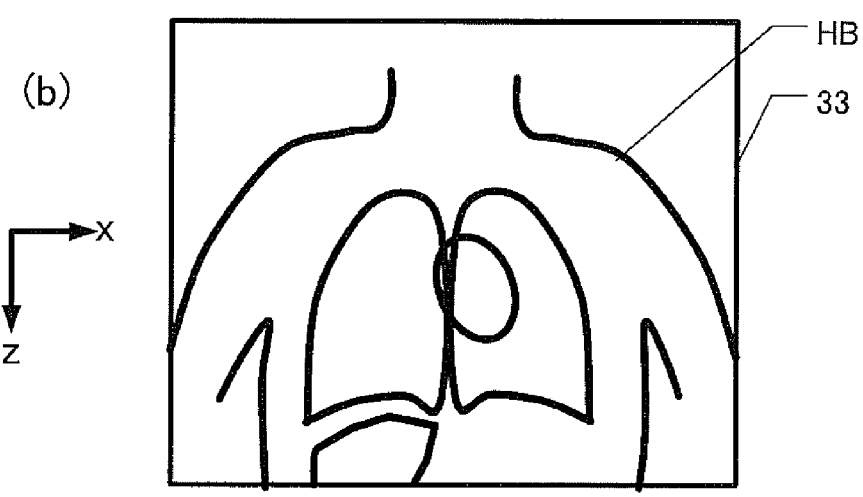

At Step S41, a comparison image of an arbitrary cross section to be diagnosed is displayed on the display 60 as shown in FIG. 4.

At Step S42, an operator defines a region of interest ROI in the displayed comparison image via the first region-of-interest defining section 23-1.

At Step S43, the first image comparison information calculating section 24-1 calculates an image characteristic quantity 165 of pixels in the region of interest ROI. Specifically, an average value of pixel values in the comparison image is calculated to determine an image characteristic quantity 165, which is displayed in the image characteristic quantity display section 27.

At Step S44, the operator adjust the weighting factor α using the weighting factor adjusting section 25-1, for example, a slider bar, while viewing the image characteristic quantity 165 displayed in the image characteristic quantity display section 27.

At Step S45, the adjusted weighting factor α causes the image characteristic quantity 165 to vary, and the whole comparison image including the region of interest ROI to vary. The operator uses the slider bar 161 to finely adjust the weighting factor α such that the image characteristic quantity 165 becomes zero or falls within a certain range from zero.

At Step S46, if the image characteristic quantity 165 becomes zero or falls within a certain range in proximity of zero, the operator presses the SET button 162 to fix the weighting factor α in the region of interest ROI.

At Step S47, the operator decides whether another region of interest ROI is to be subsequently defined. If another region of interest ROI is to be defined, the process goes back to Step S42; if all regions of interest ROI have been defined, the process goes to Step S48.

At Step S48, the dual-energy image reconstructing section 22 reconstructs a dual-energy image DI in which the region of interest ROI is made an equivalent image by the adjusted weighting factor α. As the image displayed on the display 60, the colored display section 28 displays one of the low-energy tomographic image LT or tomographic image HT of a high-energy spectrum superimposed with a colored equivalent image for facilitating diagnosis by the operator.

Automatic Weighting Factor Setting Method.

Figure 7:
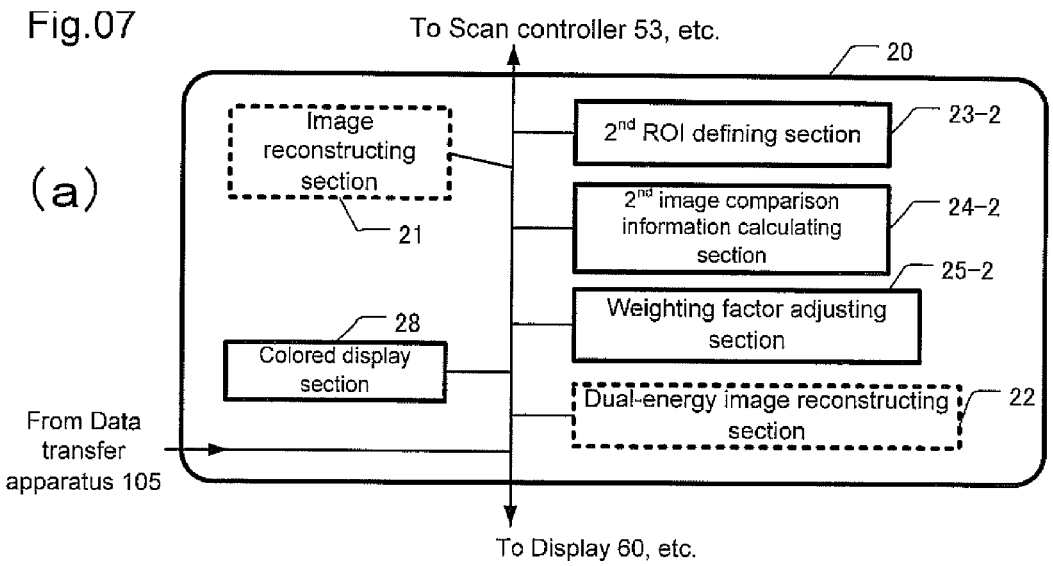
FIG. 7(a) is a block diagram of the image processing apparatus 20 for automatically setting a weighting factor.
FIG. 7(b) is a flow chart for automatically setting an appropriate weighting factor.
Figure 7:
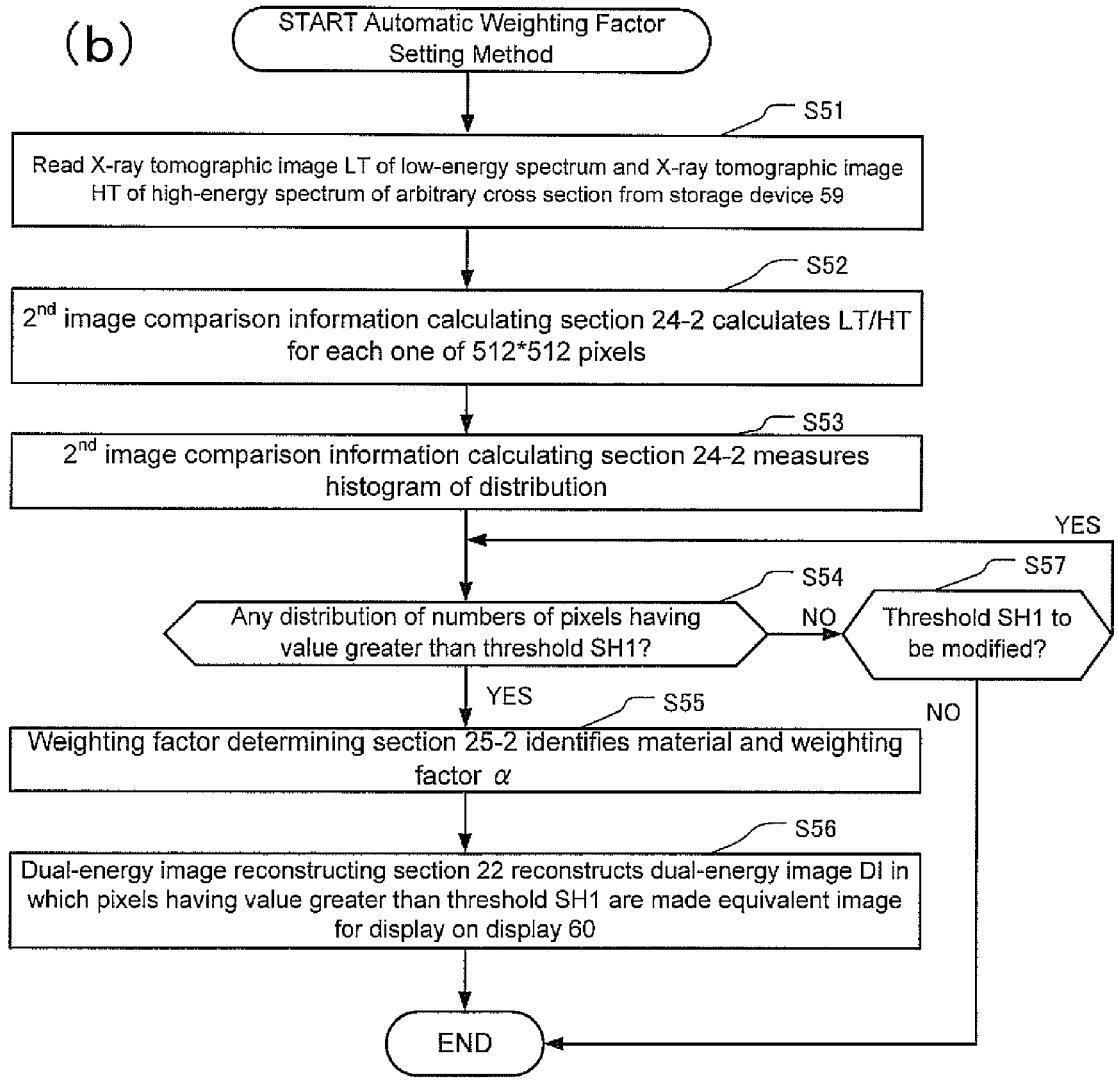

FIG. 7(a) is a block diagram of the image processing apparatus 20 for practicing an automatic weight setting method, and FIG. 7(b) is a flow chart of a method for automatically setting an appropriate weighting factor. A dual-energy image DI of an arbitrary cross section to be diagnosed is displayed on the display 60. Then, automatic weight setting is activated.

Figure 8:
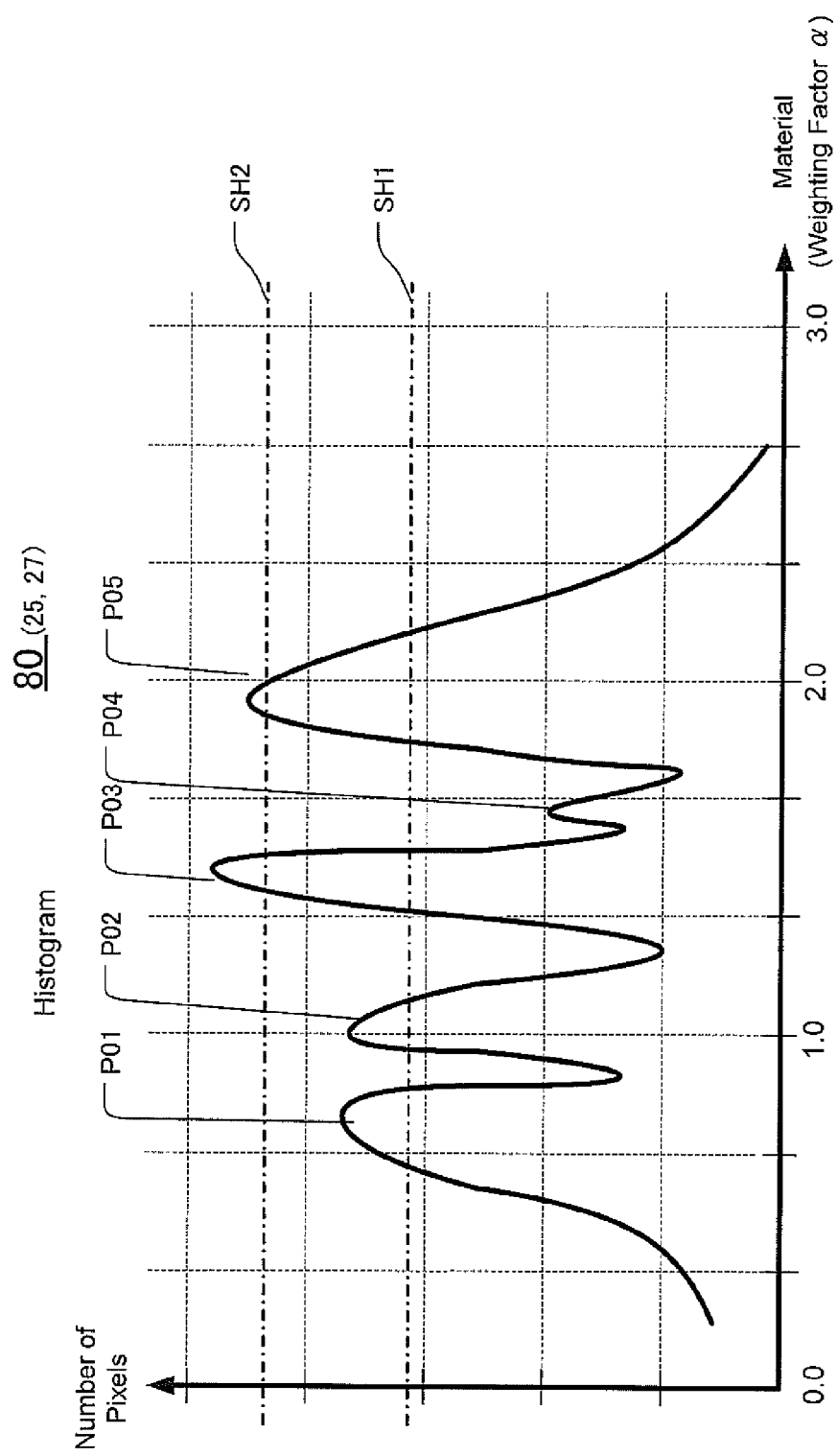
FIG. 8 is a histogram with a horizontal axis representing a ratio of an X-ray tomographic image LT of a low-energy spectrum divided by an X-ray tomographic image HT of a high-energy spectrum, and a vertical axis representing the number of pixels.

FIG. 8 is a histogram of a distribution with a horizontal axis representing a ratio of a pixel value of an X-ray tomographic image LT of a low-energy spectrum divided by that of an X-ray tomographic image HT of a high-energy spectrum on a pixel-by-pixel basis, and a vertical axis representing the number of pixels.

In automatically setting a weighting factor, the image processing apparatus 20 is comprised of the image reconstructing section 21, dual-energy image reconstructing section 22, a second region-of-interest defining section 23-2, a second image comparison information calculating section 24-2, a weighting factor determining section 25-2, and the colored display section 28, as shown in FIG. 7(a). Since the image reconstructing section 21 and dual-energy image reconstructing section 22 have been described earlier, description thereof will be omitted.

The second image comparison information calculating section 24-2 calculates a value of each pixel (512*512) in a low-energy tomographic image LT divided by that in a tomographic image HT of a high-energy spectrum, or a value of each pixel value in the tomographic image HT of a high-energy spectrum divided by that in the low-energy tomographic image LT. By thus calculating the ratio of pixel values, the second image comparison information calculating section 24-2 measures a histogram of a distribution with a horizontal axis representing the ratio of pixel values, and a vertical axis representing the number of pixels.

The second region-of-interest defining section 23-2 extracts a region having similar ratios of pixels as a region of interest from among the ratios of pixel values in the measured histogram of a distribution. In particular, the second region-of-interest defining section 23-2 defines the region of interest as containing pixels having similar ratios of pixel values around a peak value in the histogram of a distribution.

The weighting factor determining section 25-2 determines a weighting factor based on the ratio of pixel values at the peak value in the histogram of a distribution. Thus, a weighting factor for use in producing a dual-energy image is made to correspond to the extracted region of interest.

The colored display section 28 puts the same color for the same region of interest, and a different color for a different region of interest. In particular, pixels identified as fat, calcium and iodine contrast agent are colored in red, blue and green, respectively, for display on the display 60.

At Step S51, an X-ray tomographic image LT of a low-energy spectrum and an X-ray tomographic image HT of a high-energy spectrum of the current arbitrary cross section are read from the storage device 59.

At Step S52, the second image comparison information calculating section 24-2 calculates a ratio of pixels between the X-ray tomographic image LT of a low-energy spectrum and X-ray tomographic image HT of a high-energy spectrum. In general, when an X-ray tomographic image LT at a tube voltage of 80 kV and an X-ray tomographic image HT at a tube voltage of 140 kV are employed, the ratio of materials within the subject is distributed over a range from 0.5 to 2.5.

At Step S53, the second image comparison information calculating section 24-2 measures a histogram of a distribution with a horizontal axis representing the ratio of pixel values and a vertical axis representing the number of pixels. An example thereof is shown in FIG. 8. The graph as shown in FIG. 8 may be displayed on the display 60, or merely ratios of all pixels may be stored in the memory.

At Step S54, the second region-of-interest defining section 23-2 decides whether a distribution of the numbers of pixels having a value greater than a threshold SH1 is found, to thereby define a region of interest based on the distribution of the numbers of pixels having a value greater than the threshold SH1. In FIG. 8, the threshold SH1 is defined at a certain position. In FIG. 8, peaks P1, P2, P3 and P5 are greater than the threshold SH1. Thus, four distributions of the numbers of pixels are found to be greater than the threshold SH1. A peak in a portion that exceeds a threshold can be identified by differentiating the distribution of the histogram. On the other hand, the peak P4 does not exceed the threshold SH1. The peak P4, which may be caused by an influence of noise, artifacts or positional offset, can be eliminated. The second region-of-interest defining section 23-2 performs such processing to extract a region having similar ratios of pixel values as a region of interest. If one or more peaks P greater than the threshold SH1 are found, the process goes to Step S55; if no peak P greater than the threshold SH1 is found, the process goes to Step S57.

At Step S55, for a specific material at the peak P1, P2, P3 or P5 extracted by the second region-of-interest defining section 23-2, in other words, that having similar ratios of pixel values, the weighting factor determining section 25-2 fixes a weighting factor α of that specific material.

At Step S56, a dual-energy image DI in which a range around a peak P is made an equivalent image by the fixed weighting factor α is reconstructed by the dual-energy image reconstructing section 22 for display. If a plurality of peaks P are found, their respective equivalent images are calculated and the equivalent images are superimposed with each other for display. As the image displayed on the display 60, the colored display section 28 displays one of the low-energy tomographic image LT or tomographic image HT of a high-energy spectrum, superimposed with a colored equivalent image for facilitating diagnosis by the operator.

Proceeding to Step S57 means that the second region-of-interest defining section 23-2 could not extract any peak value, and therefore, the threshold SH1 is decremented. Then, the process goes back to Step S54 and a decision is made as to whether a distribution of the numbers of pixels having a value greater than the threshold SH1 is found.

Although in this embodiment, the flow chart is shown in which the threshold SH1 is decremented to search a peak P, the threshold may be incremented if a plurality of peaks P are present and the operator desires to narrow a range of materials, as in a threshold SH2.

Example of Coloring of Materials in a Dual-Energy Image DI>

Figure 9:
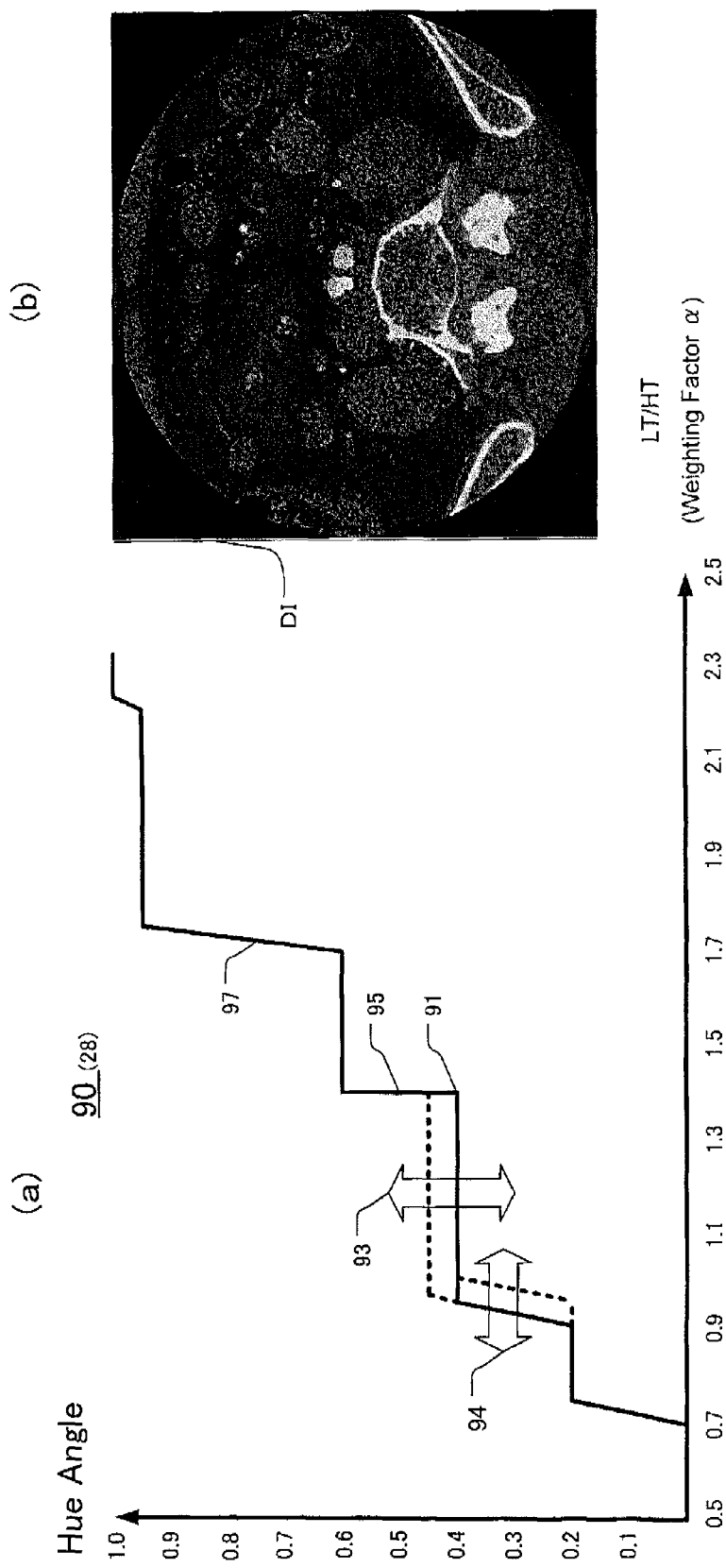
FIG. 9(a) and FIG. 9(b) are diagrams for explaining coloring of a dual-energy image DI.
Figure 10:
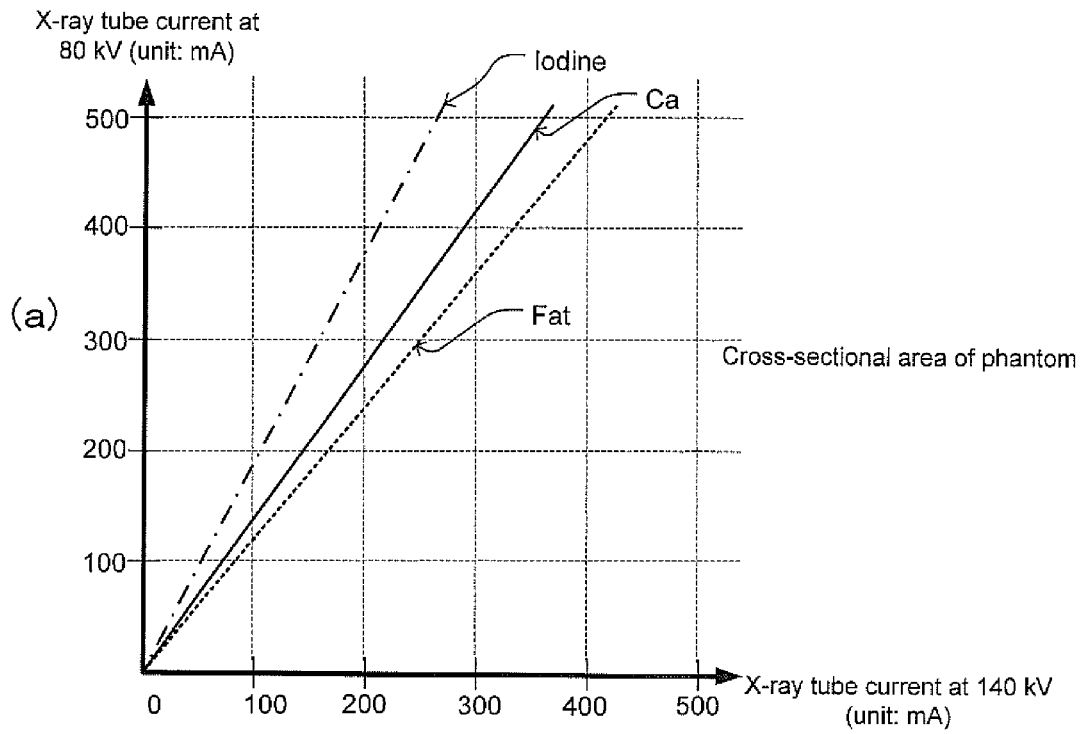
FIG. 10(a) and FIG. 10(b) are diagrams showing the relationship of the ratio of pixel values between tomographic images containing fat, calcium and iodine, obtained with low-energy X-rays and high-energy X-rays.
Figure 10:
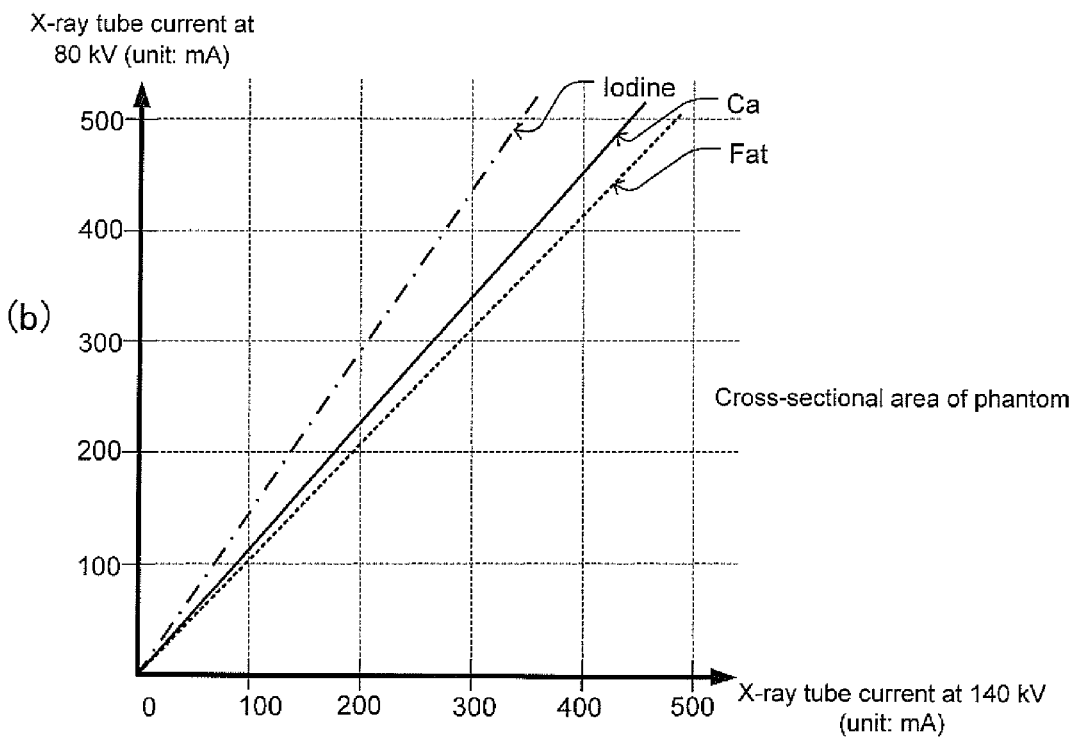

FIG. 9 is a diagram for explaining coloring by the colored display section 28 for an equivalent image.

FIG. 9(*a*) is a color map 90 in which a horizontal axis represents a ratio of pixel values between an X-ray tomographic image LT of a low-energy spectrum and an X-ray tomographic image HT of a high-energy spectrum, in other words, a weighting factor α, and a vertical axis represents a hue (a type of a color (red, blue, yellow, or the like)). Although the vertical axis is normalized to range from zero to one here, it may be expressed in an angle ranging from 0 deg. to 360 deg.

Since the horizontal axis of the color map 90 represents the weighting factor α, pixels identified as fat (α=0.8), water (α=1.0), calcium (α=1.45), and iodine contrast agent (α=1.9) are colored in red, blue, yellow and green, respectively, for facilitating perception by the operator. For example, in a graph 91 of the color map, a weighting factor α ranging from 0.95 to 1.40 is assigned with the same color. When a different color is desired to be used in the colored display section 28, the graph 91 of the color map displayed on the display 60 may be dragged by a mouse to move the graph 91 vertically in a direction indicated by an arrow 93 to a position depicted in a dotted line, thus changing the hue. Moreover, if the same color is desired to be assigned to a weighting factor α ranging from 1.00 to 1.40, the graph 91 may be dragged using the mouse to move the graph 91 horizontally in a direction indicated by an arrow 94 to a position depicted in a dotted line, thus changing the range having the same color.

Furthermore, transition in color from water to calcium is rendered by totally different hues, as shown in a portion 95 of the graph 91. On the other hand, transition in color from calcium to iodine contrast agent is rendered by a gradually changing hue, as shown in a portion 97 of the graph 91. While only a linear change is shown in FIG. 9, a non-linear hue change may be configured.

Using the thus-configured hue, specific materials are colored, and the colored specific materials are displayed in one of the low-energy tomographic image LT or tomographic image HT of a high-energy spectrum. FIG. 9(*b*) shows an example thereof.

According to the present invention, a weighting factor α for a specific material can be accurately set in a dual-energy image DI in a manual or automatic manner. Then, the specific material can be easily colored for display on the display 60. Thus, the operator can view an accurate dual-energy image DI to make diagnosis. Although in the embodiments, description has been made focusing on fat, water, calcium, iodine contrast agent, etc., it will be easily recognized that other material may be focused.

The image reconstruction technique in the embodiments may be a three-dimensional image reconstruction technique according to a conventionally known Feldkamp method. The foregoing embodiments are not particularly limited to a specific scan scheme. That is, similar effects can be obtained in any one of axial scan, helical scan, variable-pitch helical scan, and helical shuttle scan. Moreover, the scan gantry is not limited in terms of tilting. That is, similar effects can be obtained in a so-called tilted scan. Furthermore, the foregoing embodiments may be applied to cardiac image reconstruction in which an image is reconstructed in synchronization with biological signals, especially, cardiac signals.

The invention claimed is:

1. An X-ray tomographic imaging apparatus comprising:
   an image comparison information calculating section configured to calculate ratios of pixel values between a first-energy tomographic image of a subject and a second-energy tomographic image of the subject, said first-energy tomographic image reconstructed based on a first-energy projection dataset obtained using X-rays at a first energy and said second-energy tomographic image reconstructed based on a second-energy projection dataset obtained using X-rays at a second energy different than the first energy;
   a region-of-interest defining section configured to define a region of interest including a predetermined material in at least one of said first-energy tomographic image and said second-energy tomographic image;
   a weighting factor determining section configured to determine a weighting factor based on a peak value of a distribution of the ratios of pixel values; and
   a dual-energy image reconstructing section configured to reconstruct said dual-energy image by conducting a weighted subtraction processing between at least one of said first-energy projection dataset and said second-energy projection dataset and said first-energy tomographic image and said second-energy tomographic image using said weighting factor determined at said weighting factor determining section.

2. The X-ray tomographic imaging apparatus according to claim 1, wherein said region-of-interest defining section is configured to extract a region having similar ratios of pixel values as said region of interest.

3. The X-ray tomographic imaging apparatus according to claim 2, further comprising a colored display section configured to vary a color tone with the ratio of pixel values.

4. The X-ray tomographic imaging apparatus according to any claim 1, further comprising a colored display section configured to color said region of interest, and superimpose a colored region of interest over at least one of said first-energy tomographic image and said second-energy tomographic image.

5. The X-ray tomographic imaging apparatus according to claim 4, wherein said colored display section is configured to display a plurality of different regions of interest in one subject in different colors.

6. The X-ray tomographic imaging apparatus according to claim 1, wherein said region-of-interest defining section is configured to define said region of interest based on a distribution of the ratios of pixel values between said first-energy tomographic image and said second-energy tomographic image.

7. The X-ray tomographic imaging apparatus according to claim 1, wherein said region of interest comprises a region indicating at least one of fat, water, calcium, and iodine contrast agent.

8. An X-ray tomographic imaging method for reconstructing a dual-energy image of a subject, said method comprising:
   calculating ratios of pixel values between a first-energy tomographic image of the subject and a second-energy tomographic image of the subject, said first-energy tomographic image reconstructed based on a first-energy projection dataset obtained using X-rays having a first energy and said second-energy tomographic image reconstructed based on a second-energy projection dataset obtained using X-rays having a second energy different than the first energy;
   defining a region of interest including a predetermined material in at least one of said first-energy tomographic image and said second-energy tomographic image;
   determining a weighting factor based on a peak value of a distribution of the ratios of pixel values; and
   reconstructing a dual-energy image by conducting weighted subtraction processing between at least one of said first-energy projection dataset and said second-energy projection dataset and said first-energy tomographic image and said second-energy tomographic image using said weighting factor.

9. The X-ray tomographic imaging method according to claim 8, wherein defining a region of interest comprises extracting a region having similar ratios of pixel values as said region of interest.

10. The X-ray tomographic imaging method according to claim 9, further comprising displaying said image comparison information with a color tone varying with the ratio of pixel values.

11. The X-ray tomographic imaging method according to claim 8, further comprising:
    displaying at least one of said first-energy tomographic image and said second-energy tomographic image;
    coloring said region of interest; and
    superimposing a colored region of interest over at least one of said first-energy tomographic image and said second-energy tomographic image.

12. The X-ray tomographic imaging method according to claim 11, wherein coloring said region of interest comprises coloring a plurality of different regions of interest in one subject in different colors.

13. The X-ray tomographic imaging method according to claim 8, wherein defining a region of interest further comprises defining the region of interest based on a distribution of the ratios of pixel values between said first-energy tomographic image and said second-energy tomographic image.

14. The X-ray tomographic imaging method according to claim 8, wherein defining a region of interest further comprises defining the region of interest as a region indicating at least one of fat, water, calcium, and iodine contrast agent.

15. An X-ray tomographic imaging apparatus comprising:
    an image comparison information calculating section configured to calculate ratios of pixel values between a first-energy tomographic image of a subject and a second-energy tomographic image of the subject, said first-energy tomographic image reconstructed based on a first-energy projection dataset obtained using X-rays having a first energy and said second-energy tomographic image reconstructed based on a second-energy projection dataset obtained using X-rays having a second energy different than said first energy;

a region-of-interest defining section configured to define a region of interest of a predetermined material included in at least one of said first-energy tomographic image and said second-energy tomographic image based on a distribution of the ratios of pixel values;

a weighting factor determining section configured to determine a weighting factor based on a peak value of the distribution of the ratios of pixel values; and a dual-energy image reconstructing section configured to reconstruct a dual-energy image by conducting weighted subtraction processing using said weighting factor determined at said weighting factor determining section, said weighted subtraction processing conducted between at least one of said first-energy projection dataset and said second-energy projection dataset and said first-energy tomographic image and said second-energy tomographic image.

16. The X-ray tomographic imaging apparatus according to claim 15, wherein said region-of-interest defining section is configured to extract a region having similar ratios of pixel values as said region of interest.

17. The X-ray tomographic imaging apparatus according to claim 15, further comprising a colored display section configured to color said region of interest, and display a colored region of interest superimposed over at least one of said first-energy tomographic image and said second-energy tomographic image.

18. An X-ray tomographic imaging method for reconstructing a dual-energy image of a subject, said method comprising:

calculating ratios of pixel values between a first-energy tomographic image of a subject and a second-energy tomographic image of the subject, said first-energy tomographic image reconstructed based on a first-energy projection dataset obtained using X-rays having a first energy and said second-energy tomographic image reconstructed based on a second-energy projection dataset obtained using X-rays having a second energy different than said first energy;

defining a region of interest of a predetermined material included in at least one of said first-energy tomographic image and said second-energy tomographic image based on a distribution of the ratios of pixel values;

determining a weighting factor based on a peak value of the distribution of the ratios of pixel values; and reconstructing a dual-energy image by conducting weighted subtraction processing using said weighting factor, said weighted subtraction processing conducted between at least one of said first-energy projection dataset and said second-energy projection dataset and said first-energy tomographic image and said second-energy tomographic image.

19. The X-ray tomographic imaging method according to claim 18, wherein defining a region of interest further comprises extracting a region having similar ratios of pixel values as said region of interest.

20. The X-ray tomographic imaging method according to claim 18, further comprising:

coloring said region of interest; and superimposing a colored region of interest over at least one of said first-energy tomographic image and said second-energy tomographic image.

* * * * *